US009309203B2

(12) United States Patent
Wikel et al.

(10) Patent No.: US 9,309,203 B2
(45) Date of Patent: Apr. 12, 2016

(54) MALIGNANT AND NON-MALIGNANT DISEASE TREATMENT WITH RAS ANTAGONISTS

(71) Applicant: PISCES THERAPEUTICS, LLC, Rockville, MD (US)

(72) Inventors: James H. Wikel, Greenwood, IN (US); Michael J. Brownstein, Rockville, MD (US)

(73) Assignee: Pisces Therapeutics, LLC, Rockville, MD (US)

( * ) Notice: Subject to any disclaimer, the term of this patent is extended or adjusted under 35 U.S.C. 154(b) by 0 days.

(21) Appl. No.: 14/350,303

(22) PCT Filed: Oct. 5, 2012

(86) PCT No.: PCT/US2012/058900
§ 371 (c)(1),
(2) Date: Apr. 7, 2014

(87) PCT Pub. No.: WO2013/052765
PCT Pub. Date: Apr. 11, 2013

(65) Prior Publication Data

US 2014/0249163 A1 Sep. 4, 2014

Related U.S. Application Data

(60) Provisional application No. 61/544,471, filed on Oct. 7, 2011.

(51) Int. Cl.

| | |
|---|---|
| ***C07D 233/20*** | (2006.01) |
| ***A61K 31/41*** | (2006.01) |
| ***C07D 239/06*** | (2006.01) |
| ***C07D 257/04*** | (2006.01) |
| ***C07D 285/06*** | (2006.01) |
| ***C07D 333/38*** | (2006.01) |
| ***C07D 333/40*** | (2006.01) |

(52) U.S. Cl.
CPC ............ *C07D 239/06* (2013.01); *C07D 233/20* (2013.01); *C07D 257/04* (2013.01); *C07D 285/06* (2013.01); *C07D 333/38* (2013.01); *C07D 333/40* (2013.01)

(58) Field of Classification Search
CPC .. C07D 233/20; C07D 239/06; C07D 257/04; C07D 285/06
USPC ........ 544/335; 548/252, 349.1; 514/256, 381, 514/401
See application file for complete search history.

(56) References Cited

U.S. PATENT DOCUMENTS

| | | | |
|---|---|---|---|
| 5,705,528 | A | 1/1998 | Kloog |
| 6,462,086 | B1 | 10/2002 | Kloog et al. |
| 6,946,485 | B2 | 9/2005 | Kloog et al. |
| RE39,682 | E | 6/2007 | Kloog |
| 2005/0119237 | A1 | 6/2005 | Kloog et al. |
| 2007/0054886 | A1 | 3/2007 | Kloog et al. |
| 2009/0226512 | A1 | 9/2009 | Bauer |
| 2009/0226539 | A1 | 9/2009 | Kloog et al. |
| 2009/0286870 | A1 | 11/2009 | Kloog et al. |
| 2009/0298843 | A1 | 12/2009 | Kloog et al. |
| 2010/0136138 | A1 | 6/2010 | Kloog et al. |
| 2010/0189781 | A1 | 7/2010 | Kloog et al. |
| 2011/0046223 | A1 | 2/2011 | Kloog et al. |

OTHER PUBLICATIONS

Simone, Oncology: Introduction, Cecil Textbook of Medicine, 20th Edition, vol. 1, pp. 1004-1010, 1996.*

Gura, Systems for identifying New Drugs Are Often Faulty, Cancer Models, Science, vol. 278, No. 5340, pp. 1041-1042, Nov. 1997.*

Johnson et al., Relationships between drug activity in NCI preclinical in vitro and in vivo models and early clinical trials, British Journal of Cancer (2001) 64(10): 1424-1431.*

Pearce et al., Failure modes in anticancer drug discovery and development, Cancer Drug Design and Discovery Edited by Stephen Neidle, Chapter 18, pp. 424-435 (2008).*

Wang et al., Ras inhibition via direct Ras binding—is there a path forward?, Bioorganic & Medicinal Chemistry Letters, vol. 22, pp. 5766-5776 (2012).*

Nussinov et al., Pathway drug cocktail: targeting Ras signaling based on structural pathways, Trends in Molecular Medicine, vol. 19, Issue 11, pp. 695-704, Nov. 2013.*

Roskoski, A historical overview of protein kinases and their targeted small molecule inhibitors, Pharmacological Research, vol. 100, pp. 1-23 (2015).*

International Search Report and Written Opinion issued by the ISA/US Commissioner for Patents, dated Nov. 16, 2012, for International PCT Application No. PCT/US2012/058900; 13 pages.

Supplementary European Search Report for EP12838578, dated Mar. 12, 2015, 7 pages.

Ferri N. et al., "Isothiazole dioxide derivative 6n inhibits vascular smooth muscle cell proliferation and protein farnesylation", Biochemical Pharmacology, 70(12), Dec. 5, 2005, pp. 1735-1743, XP027715449; 9 pages.

Marom M. et al., "Minimal Structural Requirements for Diglyceride-Site Directed Activators of Protein Kinase C", Tetrahedron, 53(29), Jul. 1, 1997, pp. 10041-10050, XP004106122; 10 pages.

Egan, S. E. and Weinberg, R.A., "The Pathway to Signal Achievement", 365, pp. 781-782; Oct. 28, 1993; 3 pages.

(Continued)

*Primary Examiner* — Deepak Rao
(74) *Attorney, Agent, or Firm* — Faegre Baker Daniels LLP

(57) ABSTRACT

The present disclosure describes new inhibitors or antagonists of Ras useful for the treatment of conditions resulting from Ras-induced or mediated cellular processes, including cellular proliferation, differentiation, apoptosis, senescence, and survival. These cellular processes may be associated with a non-malignant or malignant disease, disorder, or pathological condition. The present disclosure also describes a method for inhibiting such Ras-induced or mediated cellular processes. The method entails administering a Ras antagonist in an amount effective to inhibit such cellular processes.

16 Claims, 5 Drawing Sheets

(56) References Cited

OTHER PUBLICATIONS

McCormick, F., "How Receptors Turn Ras on", Nature, 363, pp. 15-16; May 6, 1993; 2 pages.
Zheng, X. F. et al., "Normal and Oncogenic p2lras Proteins Bind to the Amino-terminal Regulatory Domain of c-Raf-1", Nature, 364, pp. 308-313; Jul. 22, 1993; 6 pages.
Warne, P. H., "Direct Interaction of Ras and the Amino-Terminal Region of Raf-1 in vitro", Nature, 364, pp. 352-355; Jul. 22, 1993; 4 pages.
Bos, J. L. Cancer Research, "ras Oncogenes in Human Cancer: A Review", 49, pp. 4682-4689; Sep. 1, 1989; 9 pages.
Barbacid, M., "ras Genes", Am. Rev. Biochem., 56, pp. 779-829 (1987); 49 pages.
Lin F., Baldassare, J.J., Voorhees, J.J., Fisher, G.J., "Increased Activation of Ras in Psoriatic Lesions", Skin Pharmacol Appl Skin Physiol Jan.-Apr. 1999;12(1-2): pp. 90-97; 8 pages.
Mark, E.B., Jonsson, M., Asp, J., Wennberg, A.M., Molne, L., Lindahl, A., "Expression of genes involved in the regulation of p16 in psoriatic involved skin", Arch Dermatol Res Apr. 2006;297(10): pp. 459-467; 9 pages.
Parker, E., Newby, L.J., Shaprpe, C.C., Rossetti, S., Streets, A.J., Harris, P.C., O'Hare, M.J., Ong, A.C., "Hyperproliferation of PKD1 cystic cells is induced by insulin-like growth factor-1 activation of the Ras/Raf signaling system", Kidney Int Jul. 2007:72(2): pp. 157-165; 9 pages.
Trujillo, J.I., "MEK Inhibitors: a Patent Review 2008-2010", Expert IPIN Ther. Pat. 21, pp. 1045-1069 (2011); 25 pages.
Svegliati S, Olivieri A, Campelli N, Luchetti M, Poloni A, Trappolini S, Moroncini G, Bacigalupo A, Leoni P, Avvedimento EV, and Gabrielli A., "Stimulatory autoantibodies to PDGF receptor i patients with extrensive chronic graf-oversus-host disease", BLOOD, 110, pp. 237-241; Jul. 1, 2007; 6 pages.
Mor, A., Aizman, E., George, J., Kloog, Y., "Ras Inhibition induces insulin sensitivity and glucose uptake", PLoS ONE 2011 6(6):e21712; 11 pages.
George, J., Afek, A., Keren, P., Herz, I., Goldberg, I., Haklai, R., Kloog, Y., Keren, G., "Functional inhibition of Ras by a Ras antagonist attenuates atherosclerosis in apolipoprotein E knockout mice", Circulation. 2002, 105(20); pp. 2416-2422; 8 pages.
Satoh T. and Kaziro Y., "Ras in Signal Transduction" (1992). Cancer Biol., 3, pp. 169-177; 9 pages.
Kloog, et al., "Concepts in Ras-odirected Therapy", Exp. Opin. Invest. Drugs (1999) 8(12):2121-2140; 20 pages.
Khosravi-Far R and Der CJ. (1994). Cancer Metastasis Rev. 13, pp. 67-89; 23 pages.

* cited by examiner

MALIGNANT AND NON-MALIGNANT DISEASE TREATMENT WITH RAS ANTAGONISTS

CROSS REFERENCE TO RELATED APPLICATIONS

This application is a U.S. national stage application based on PCT Application No. PCT/US2012/058900, filed Oct. 5, 2012, which claims priority from U.S. Provisional Patent Application Serial No. 61/544,471, filed Oct. 7, 2011, the disclosures of which are hereby expressly incorporated by reference herein in their entirety.

FIELD OF THE DISCLOSURE

The present disclosure relates to the treatment of malignant and non-malignant (i.e., benign) diseases, disorders, or pathological states with Ras antagonists.

BACKGROUND OF THE DISCLOSURE

Ras is a membrane-associated guanine-nucleotide-binding protein that plays a key role in many cellular processes, including cell proliferation, apoptosis, differentiation, senescence, and survival. Ras is an ON-OFF switch for such cellular processes. While it is normally at rest (OFF) and bound to the guanosine diphosphate (GDP) nucleotide, Ras can be activated (ON) when bound to the guanosine triphosphate (GTP) nucleotide by extracellular signaling molecules that act on a variety of targets.

Ras proteins play a key role in tyrosine kinase growth-factor receptor signaling (Egan, S. E. and Weinberg, R. A. Nature 365, 781-782 (1993); McCormick, F., Nature, 363, 15-16 (1993)). When activated in the GTP-bound form, Ras proteins propagate the growth factors' signal to the MAP kinase cascade. Ras proteins are associated with the plasma membrane where activation of the Raf kinase occurs through a direct Ras/Raf interaction (Zheng, X. F. et al., Nature, 364, 308-313 (1993); Warne, P. H., Nature, 364, 352-353 (1993)).

Termination of growth factor signaling involves hydrolysis of the active, GTP-bound form of Ras to the inactive, GDP-bound form of Ras. However, mutated or oncogenic Ras proteins do not hydrolyze GTP and are therefore in a permanently active (ON) state. The inability to hydrolyze GTP may contribute to various uncontrolled cellular functions.

Activated Ras can initiate and drive malignant cell growth of tumor cells, including tumor cells that express activated Ras proteins. Mutated Ras proteins are found at high frequencies in human cancers (Bos, J. L. Cancer Res., 49, 682-4689 (1989); Barbacid, M., An. Rev. Biochem, 56, 779-829 (1987)). In some types of tumors, such as colon and pancreatic carcinomas, the incidence of activated Ras is higher than 50%. In addition to tumors that result from the unbridled actions of mutated or oncogenic Ras, there are also tumors that are caused by constitutively active growth factor receptors (e.g., the Epidermal Growth Factor receptor, the Fibroblast Growth Factor receptor, and the Platelet-Derived Growth Factor receptor) that hold Ras in the active (ON) position. Therefore, pharmacological methods to affect Ras activity may be of use for the treatment of certain types of human cancers.

In addition to malignant cancer, activated Ras can initiate and drive non-malignant (i.e., benign) cellular proliferation. One example of Ras-induced, non-malignant cellular proliferation is psoriatic lesions. An increased level of activated Ras has been found in psoriatic lesion of patients. (Lin F., Baldassare, J. J., Voorhees, J. J., Fisher, G. J. Increased activation of Ras in psoriatic lesions Skin Pharmacol Appl Skin Physiol 1999 January-April; 12(1-2):90-7). In addition, receptor signaling via the Ras/MAPK cascade has been identified as playing a key role in psoriatic lesions (Mark, E. B., Jonsson, M., Asp, J., Wennberg, A. M., Molne, L., Lindahl, A. Expression of genes involved in the regulation of p16 in psoriatic involved skin. Arch Dermatol Res 2006 April; 297(10):459-67. Epub 2006 Mar. 22).

Other examples of Ras-induced, non-malignant cellular proliferation are found in a variety of inherited diseases (e.g., neurofibromatosis type 1 (NF-1) and polycystic kidney disease (PKD)) and diverse sporadic problems such as hepatic, renal, and cardiac fibrosis. For example, neurofibromin is a protein that will turn off Ras and is therefore a tumor suppressor. A genetic mutation leading to the absence or loss of neurofibromin leads to NF-1, a condition where tumors grow on the nerve tissue. These tumors may be non-malignant (i.e., benign), but depending on their location, they may cause serious damage to surrounding tissues. In addition, these tumors may transform into malignant conditions such as neurofibrosarcoma or leukemia. As another example, autosomal dominant PKD is a proliferation of renal epithelial cells and subsequent cyst formation. Inhibition of Ras stops the aberrant growth of these cells. (Parker, E., Newby, L. J., Shaprpe, C. C., Rossetti, S., Streets, A. J., Harris, P. C., O'Hare, M. J., Ong, A. C. Hyperproliferation of PKD-1 cystic cells is induced by insulin-like growth factor-1 activation of the Ras/Raf signaling system. Kidney Int 2007 July: 72(2): 157-65. Epub 2007 Mar. 28).

Still another example of Ras-induced, non-malignant cellular proliferation is found in the pathological state of post-angioplasty restenosis following the placement of stents in arteries, which results from the proliferation of vascular endothelial cells. Such cell proliferation may be initiated by tissue injury or damage (e.g., damage caused by insertion of the stent) or local vascular inflammation, for example.

In addition to driving cellular proliferation and tumorigenesis, Ras activation mediates a number of immune phenomena and abnormalities in immune function, such as those seen in autoimmune diseases. These autoimmune diseases can be Ras dependent. Autoimmune diseases are characterized by self-inflicted tissue damage. Any organ may be affected by such processes through precipitation of immune complexes, cellular immunity, or inappropriate generation or action of proinflammatory immuno-hormones such as cytokines Autoimmune diseases are a significant public health problem because of the numbers of patients that they affect and the morbidity and mortality that they cause. Common chronic systemic diseases in this group include type 1 diabetes mellitus, Hashimoto's thyroiditis, rheumatoid arthritis, systemic lupus erythematosus (SLE), primary antiphospholipid syndrome (APS), and a variety of diseases that affect the central and peripheral nervous systems, including myasthenia gravis, Lambert Eaton myasthenic syndrome, Guillain-Barre syndrome, polymyositis, and multiple sclerosis. In addition, there are neurological complications of the systemic autoimmune diseases. The sensory neuropathy associated with type 1 diabetes is an example. Factors contributing to autoimmune diseases include genetic predisposition and environmental agents (e.g., certain infections and pharmaceutical products). The rejection of cells and tissues following organ transplantation is another immune system mediated phenomenon in which Ras has been implicated (Trujillo, J. I., Expert Ipin Ther Pat. 21, 1045-1069 (2011)), as is chronic graft versus host disease (Svegliati S, Olivieri A, Campelli N, Luchetti M, Poloni A, Trappolini S, Moroncini G, Bacigalupo A, Leoni P, Avvedimento E V, and Gabrielli A. Blood 110, 237-241 (2007).

Just as abnormalities in Ras signaling drive pathological immune responses, activated Ras can contribute to the dysregulation of other body systems as well, such as the endocrine system and the vascular system. An example is the faulty control of insulin sensitivity in peripheral tissues and ultimately the failure of the pancreas in type 2 diabetes. Ras antagonists can reverse insulin resistance in animal models of this disease. (Mor, A., Aizman, E., George, J., Kloog, Y. Ras Inhibition induces insulin sensitivity and glucose uptake. PLoS One 2011 6(6):e21712. Epub 2011 Jun. 29). Another example is vascular inflammation which is driven by proinflammatory adipokines in obese animals and humans and which contributes to the pathology of diabetes and atherosclerosis. (George, J., Afek, A., Keren, P., Herz, I., Goldberg, I., Haklai, R., Kloog, Y., Keren, G. Functional inhibition of Ras by a Ras antagonist attenuates atherosclerosis in apolipoprotein E knockout mice. Circulation 2002, 105(20): 2416-2422).

SUMMARY

The present disclosure describes new inhibitors or antagonists of Ras useful for the treatment of conditions resulting from Ras-induced or mediated cellular processes, including cellular proliferation, differentiation, apoptosis, senescence, and survival. These cellular processes may be associated with a non-malignant or malignant disease, disorder, or pathological condition.

The present disclosure also describes a method for inhibiting such Ras-induced or mediated cellular processes. The method entails administering a Ras antagonist in an amount effective to inhibit such cellular processes.

The Ras family of oncogenes is an important component in many cellular signaling networks Inhibitors of such cellular signaling would result in both upstream signaling and downstream effector pathways providing functional control of such cellular processes.

In addition to malignant cancers, such as pancreatic cancer, leukemia, Merkel cell carcinoma, and glioblastoma, the present disclosure is particularly applicable to diverse non-malignant diseases characterized by proliferation of cells, including cirrhosis of the liver, restenosis of vessels following the placement of stents, PKD, and psoriasis. Because Ras activation drives dysfunction of the immune system, the antagonists of the present disclosure can also be used to treat autoimmune diseases, such as type 1 diabetes, lupus, rheumatoid arthritis, and multiple sclerosis, and pathological states such as graft rejection induced by the presentation of a foreign antigen (e.g., a graft) in response to a disease condition (e.g., kidney failure). Similarly, the antagonists of the present disclosure can be employed to treat Ras-mediated abnormalities in endocrine organs (e.g., type 2 diabetes) and blood vessels (e.g., arteriosclerosis).

According to an exemplary embodiment of the present disclosure, a Ras antagonist is provided according to the Formula (I):

$$R^1—R^2—R^3—R^4 \quad (I)$$

wherein $R^3$ represents S, O, N, SO, $SO_2$, or Se, and $R^4$ represents farnesyl or geranyl-geranyl, and wherein at least one of $R^2$ represents a 5-membered heterocyclic ring with at least one heteroatom, and $R^1$ represents a 5- or 6-membered heterocyclic ring with at least one heteroatom. The heteroatoms of $R^2$ or $R^1$ may be selected from the group consisting of O, N, S, SO, and $SO_2$.

In embodiments in which $R^2$ represents a 5-membered heterocyclic ring with one or two heteroatoms, $R^1$ may represent CN, $C(=O)R^5$, $S(=O)(=O)R^5$, $CO_2M$, $SO_3M$, or an $N(R^8)$—substituted tetrazole, wherein: $R^5$ represents hydrogen, hydroxyl, C1-C4 alkyloxy, C2-C4 alkenyloxy, C1-C4 hydroxyalkyloxy, C1-C4 aminoalkyloxy, or $NR^6R^7$; $R^6$ represents hydrogen, hydroxyl, C1-C4 alkyl, C2-C4 alkenyl, C1-C4 aminoalkyl, C1-C4 hydroxyalkyl, C1-C4 alkyloxy, or C1-C4 alkylamino, and $R^7$ represents hydrogen, C1-C4 alkyl, C2-C4 alkenyl, C1-C4 aminoalkyl, C1-C4 hydroxyalkyl, C1-C4 alkyloxy, or C1-C4 alkylamino, or $R^6$ and $R^7$ together form a ring including morpholine, piperazine, or piperidine; M is a salt forming organic or inorganic counter ion; and $R^8$ represents hydrogen or C1-C4 alkyl. An exemplary Ras antagonist includes compound (3) below, and analogs thereof.

In embodiments in which $R^1$ represents a 5- or 6-membered heterocyclic ring with at least one heteroatom, $R^2$ may represent a phenyl ring or an optionally substituted phenyl ring. $R^1$ may represent imidazoline, imidazole, pyrazole, pyrrole, oxazole, thiazole, 1,4,5,6-tetrahydropyrimidine, triazole, or $N(R^9)$-substituted tetrazole, wherein $R^9$ represents hydrogen or C1-C4 alkyl; the optionally substituted phenyl ring is substituted with Cl, Br, F, I, C1-C4 alkyl, or C1-C4 alkoxy, amino, mono- or di-substituted amino; and the nitrogen substitutent on the phenyl ring is C1-C4 alkyl. Exemplary Ras antagonists include compounds (1), (5), and (9) below, and analogs thereof.

In embodiments in which $R^2$ represents a 5-membered heterocyclic ring with at least three heteroatoms, $R^1$ may represent $C(=O)R^{10}$, wherein $R^{10}$ represents hydrogen, hydroxyl, or C1-C4 alkyloxy. $R^2$ may represent a thiadiazole group or an oxadiazole group, for example. An exemplary Ras antagonist includes compound (4) below, and analogs thereof.

According to another exemplary embodiment of the present disclosure, a method is provided for inhibiting Ras-induced proliferation of cells associated with a malignant or non-malignant disease or pathological state. The method includes administering to a patient the Ras antagonist of Formula (I) in an amount effective to inhibit the proliferation. The administering step may be performed parenterally, orally, topically, intranasally, nasally, buccally, or transdermally. In one embodiment, the patient is afflicted with dysregulation of the immune system resulting in at least one of systemic lupus erythematosis (SLE), multiple sclerosis (MS), antiphospholipid syndrome (APS), rheumatoid arthritis, type 1 diabetes, organ rejection, and chronic graft vs. host disease. In another embodiment, the patient is afflicted with dysregulation of at least one of the endocrine system and targets of endocrine hormones resulting in type 2 diabetes. In another embodiment, the patient is afflicted with at least one of tissue injury, tissue damage, and local vascular inflammation resulting in atherosclerosis.

According to yet another exemplary embodiment of the present disclosure, a method is provided for inhibiting Ras-induced proliferation of cells associated with a malignant disease or pathological state. The method includes contacting the cells with the Ras antagonist of Formula (I) in an amount effective to inhibit the proliferation. The malignant disease may include gliobastoma, adenocarcinoma, soft tissue sarcoma, and/or leukemia.

According to yet another exemplary embodiment of the present disclosure, a method is provided for inhibiting Ras-induced proliferation of cells associated with a non-malignant disease or pathological state. The method includes contacting the cells with the Ras antagonist of Formula (I) in an amount effective to inhibit the proliferation. The non-malignant disease may include psoriasis, neurofibromatosis type 1 (NF-1), malignant tumors associated with NF-1, polycystic kidney disease (PKD), postangioplasty restenosis, tissue fibrosis, and/or muscular dystrophy.

According to still yet another exemplary embodiment of the present disclosure, a method is provided for inhibiting Ras-induced proliferation of cells. The method includes contacting the cells with the Ras antagonist of Formula (I) in an amount effective to inhibit the proliferation, wherein the proliferation is initiated by tissue injury or tissue damage.

BRIEF DESCRIPTION OF THE DRAWINGS

The above-mentioned and other features and advantages of this disclosure, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 1:
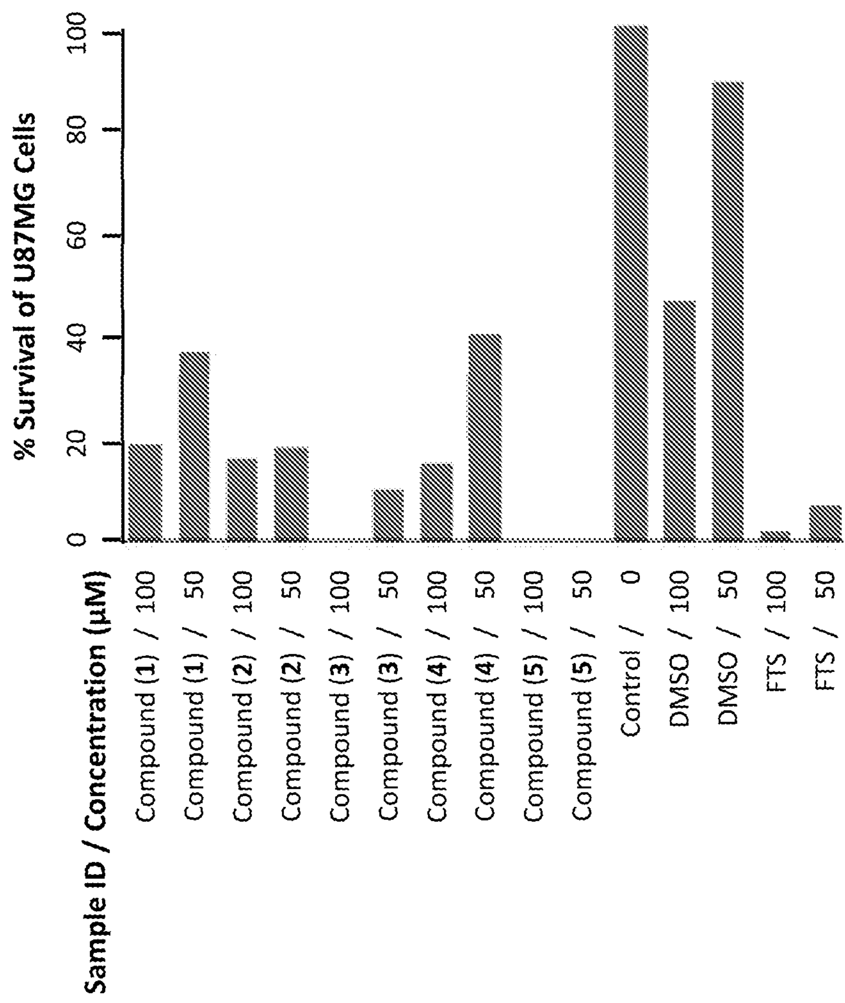
FIG. 1 is a graph illustrating the inhibition of U87MG cell proliferation relative to a control sample when exposed to certain inventive compounds of the present disclosure in various doses.

The general chemical terms used in the formula described have their usual meaning. For example, the term "C1-C4 alkyl" includes methyl, ethyl, propyl, isopropyl, butyl, isobutyl, sec-butyl, and tert-butyl. The term "C1-C4 alkyloxy" is taken to mean a C1-C4 alkyl group linked to the parent molecule through an oxygen atom and includes the groups methoxy, ethoxy, isopropoxy, and the like. The term "C2-C4 alkenyl" includes vinyl, allyl, and crotyl. The term "C1-C4 aminoalkyl" is taken to mean a C1-C4 alkyl group attached to the parent molecule via one carbon atom with a nitrogen atom attached to one distal carbon atom and includes the groups aminomethylene, aminoethylene, aminopropylene, alpha-aminoethylene, beta-aminoethylene, and the like. The term "C1-C4 hydroxyalkyl" is taken to mean a C1-C4 alkyl group attached to the parent molecule via one carbon atom with an oxygen atom attached to one distal carbon atom and includes the groups hydroxymethylene, hydroxyethylene, hydroxypropylene, alpha-hydroxyethylene, beta-hydroxyethylene, and the like. The term amino refers to a nitrogen atom attached to the parent structure and optionally substituted with one (designated by the term "mono-") or two (designated by the term "di-") additional chemical moiety or moieties which, when taken together, may form a ring such as morpholine or piperidine, or piperazine. The term "C1-C4 alkylamino" is taken to mean a C1-C4 alkyl group linked to the parent molecule through a nitrogen atom and includes the groups methylamine, ethylamine, isopropylamine, butylamine, isobutylamine, sec-butylamine, and tert-butylamine. The term "C2-C4 alkenyloxy" is taken to mean a C2-C4 alkenyl group linked to the parent molecule through an oxygen atom and includes the groups vinyloxy, allyloxy, and crotyloxy. The term "C1-C4 hydroxyalkyloxy" is taken to mean a C1-C4 alkyl group linked to the parent molecule through an oxygen atom with an oxygen atom attached to one distal carbon atom and includes the groups hydroxymethoxy, hydroxyethoxy, hydroxypropoxy, beta-hydroxyethoxy, and the like. The term "C1-C4 aminoalkyloxy" is taken to mean a C1-C4 alkyl group linked to the parent molecule through an oxygen atom with a nitrogen atom attached to one distal carbon atom and includes the groups alpha-hydroxymethylamine, beta-hydroxyethylamine, gamma-hydroxypropylamine, beta-hydroxyethylamine, and the like.

The skilled artisan will appreciate that certain compounds of Formula I may exist as the geometric cis- and trans-isomers. The present disclosure contemplates all individual isomers as well as mixtures of the geometric isomers of said compounds. It is preferred that compounds of Formula I exist as single geometric isomers. The skilled artisan will recognize the individual isomers may be prepared selectively by known methods or the mixtures of isomers may be separated by standard chromatographic or crystallization techniques, for example.

The skilled artisan will appreciate that certain compounds of Formula I may exist which contain at least one chiral center. The present invention contemplates all individual enantiomers or diastereomers, as well as mixtures of the enantiomers and diastereomers of said compounds, including racemates. It is preferred that compounds of Formula I containing at least one chiral center exist as single enantiomers or diastereomers. The single enantiomers or diastereomers may be prepared beginning with chiral reagents or by stereoselective or stereospecific synthetic techniques. Alternatively, the single enantiomers or diastereomers may be isolated from mixtures by standard chromatographic or crystallization techniques.

The skilled artisan will appreciate that certain compounds of Formula I may exist as tautomers. The present disclosure contemplates all tautomeric forms.

It will be understood by the skilled reader that certain compounds of Formula I may be capable of forming salts. In all cases, the pharmaceutically acceptable salts of all the compounds are contemplated. When the compounds of the present disclosure include amines, for example, the compounds may react with any number of inorganic or organic acids to form pharmaceutically acceptable addition salts.

It will be understood by the skilled reader that pharmaceutically acceptable solvates of compounds of Formula I are contemplated as part of this disclosure and may be prepared by conventional methods such as dissolving the compound of Formula I in a suitable solvent (e.g., water, methanol, ethanol, etc.) and recrystallizing the solute by using different crystallization techniques. Alternatively, excess solvent may be removed by evaporation to provide the solvates.

The term "Ras" is taken to mean the three gene products in the Ras superfamily of proteins designated as hRas, kRas, and nRas.

The term "Ras antagonist" is taken to mean a compound or agent that targets one or more cellular processes, including cellular proliferation, differentiation, apoptosis, senescence, and survival, to reduce, suppress, or inhibit such cellular processes (Satoh T and Kaziro Y. (1992). Cancer Biol., 3, 169±177; Khosravi-Far R and Der C J. (1994). Cancer Metastasis Rev. 13, 67-89). Ras proteins are the ON/OFF switch between hormone/growth factor receptors and the regulatory cascades that stimulate cell division. For Ras to be activated (ON), it must be attached to the inside of the cell membrane. Therefore, in one embodiment, the Ras antagonist of the present disclosure interrupts the association of Ras with the cell membrane, thereby blocking activation of Ras or inhibiting activated Ras (Kloog, et al., Exp. Opin. Invest. Drugs 8(12):2121-2140 (1999)).

The present disclosure is directed to the treatment of malignant diseases, disorders, or pathological conditions that feature or otherwise include Ras-induced cellular functions. Mutations in the Ras genes have been identified in approximately 30% of all human tumors. Examples of these malignant conditions include, for example: adenocarcinomas including pancreatic, cervix, colon, prostate, and stomach; carcinomas including bladder, breast, liver, lung, skin (e.g., Merkel cell carcinoma), and thyroid; leukemias including acute myeloid leukemia (AML), chronic myeloid leukemia (CML), chronic myelomonocytic leukemia (CMML), and juvenile myelomonocytic leukemia (JMML); soft tissue sarcomas including angiosarcoma, leiomyosarcoma, liposarcoma, rhadbomyosarcoma, and myxoma; and blastomas including kidney, liver, and brain (e.g., glioblastoma).

Additionally, the present disclosure is directed to the treatment of non-malignant diseases, disorders, or pathological conditions that feature or otherwise include Ras-induced cellular functions. Activated Ras can initiate and drive non-malignant cellular proliferation as seen in psoriasis, for example. Activated Ras is seen in a variety of inherited diseases, such as NF-1 and PKD Inhibitors of Ras may also be useful in the treatment of various familial developmental syndromes where mutations have occurred in the Ras signaling pathways. Additional examples of these disorders would include, for example, Leopard syndrome, Noonan syndrome, Legius syndrome, Costello syndrome, Cardio-faciocutaneous syndrome, Hereditary gingival fibromatosis type 1, Autoimmune lymphoproliferative syndrome, and Capillary malformation-arteriovenous malformation. In postangioplasty restenosis the insertion of an intra-arterial stent causes damage, release of growth factors and proliferation of normal smooth muscle cells. An additional example includes cirrhosis of the liver, which involves proliferation of normal hepatocytes, stellate cells and connective tissue cells. Additional examples of Ras activated cell proliferation include diverse sporadic problems such as tissue fibrosis, including hepatic, renal, and cardiac fibrosis (e.g., myocardial fibrosis), which may be seen in end-stage kidney disease, cirrhosis of the liver, and muscular dystrophy, for example.

Furthermore, the present disclosure is directed to the treatment of Ras activated or mediated immune phenomena and abnormalities in immune function, such as those seen in autoimmune diseases. Common chronic systemic diseases in this group include type 1 diabetes mellitus, Hashimoto's thyroiditis, rheumatoid arthritis, systemic lupus erythematosus (SLE), primary antiphospholipid syndrome (APS), and a variety of diseases that affect the central and peripheral nervous systems, including myasthenia gravis, Lambert Eaton myasthenic syndrome, Guillain-Barre syndrome, polymyositis, and multiple sclerosis (MS). In addition, there are neurological complications of the systemic autoimmune diseases. The sensory neuropathy associated with type 1 diabetes is an example. Factors contributing to autoimmune diseases include genetic predisposition and environmental agents (e.g., certain infections and pharmaceutical products). The chronic rejection of cells and tissues following organ transplantation is another immune system mediated phenomenon. Graft rejection is a disorder that involves the recognition of foreign cells by the immune system of the recipient ("the host") and is also known as graft vs. host disease. To attack such cells is an appropriate immune response, but following organ transplantation, this is actually detrimental to the host.

Additionally, the present disclosure is directed to the treatment of Ras-activated or mediated phenomena, and dysregulation of the endrocrine function such as those seen in type 2 diabetes. In type 2 diabetes, there exists faulty control of insulin sensitivity in peripheral tissues and, ultimately, the failure of the pancreas.

Furthermore, the present disclosure is directed to the treatment of category of diseases initiated by Ras-mediated tissue inflammation and damage, such as local vascular inflammation and damage. Vascular inflammation, which is driven by proinflammatory adipokines in obese animals and humans, contributes to the pathology of diabetes and atherosclerosis.

The Ras antagonist of the present disclosure is represented by Formula I below:

$$R^1—R^2—R^3 \mathbf{13}\, R^4 \quad \text{(I)}$$

wherein:

$R^3$ represents S, O, NH or a substituted N, SO, $SO_2$, or Se; and $R^4$ represents famesyl or geranyl-geranyl.

Formula (I) may be described as a prenyl derivative of carboxylic acids and molecular structures resembling the carboxyl-terminal farnesylcysteine common to oncogenic Ras proteins. Such agents competitively block intracellular signaling through the Ras cascade and are therefore useful for the treatment of, for example, cancer. The present disclosure describes, in particular, the use and preparation of farnesyl, geranyl-geranyl-aryl and geranyl-geranyl-heteroaryl analogs of the general Formula (I). These types of agents are known to competitively block intracellular signaling through the Ras cascade and are therefore useful for the treatment of, for example, cancer.

According to a first exemplary embodiment of the present disclosure, Formula (I) is further defined as set forth below:

$R^2$ represents a 5-membered heterocyclic ring with one or two heteroatoms, such as O, N, S, SO, and $SO_2$; and $R^1$ represents CN or one of the groups: $C(=O)R^5$, $S(=O)(=O)R^5$, $CO_2M$, $SO_3M$, and an $N(R^8)$-substituted tetrazole:

wherein:

$R^5$ represents hydrogen, hydroxyl, C1-C4 alkyloxy, C2-C4 alkenyloxy, C1-C4 hydroxyalkyloxy, C1-C4 aminoalkyloxy, or $NR^6R^7$;

$R^6$ represents hydrogen, hydroxyl, C1-C4 alkyl, C2-C4 alkenyl, C1-C4 aminoalkyl, C1-C4 hydroxyalkyl, C1-C4 alkyloxy, or C1-C4 alkylamino, and $R^7$ represents hydrogen, C1-C4 alkyl, C2-C4 alkenyl, C1-C4 aminoalkyl, C1-C4 hydroxyalkyl, C1-C4 alkyloxy, or C1-C4 alkylamino, or wherein $R^6$ and $R^7$ together form a ring such as morpholine, piperazine, or piperidine;

M is a salt forming organic or inorganic counter ion such as, but not limited to, sodium, potassium, an organic amine or a solublizing organic substance as N-alkylated glucamines prepared from glucose and an alkylamine, for example, N-methylglucamine wherein the alkylamine is C1-C4; and $R^8$ represents hydrogen or C1-C4 alkyl.

Based on this first exemplary embodiment, Formula (I) may include, for example, 3-{[(2E,6E)-3,7,11-trimethyldodeca-2,6,10-trien-1-yl]sulfanyl}thiophene-2-carboxylic acid (3) (shown below) and its analogs, wherein $R^1$ is a carboxylic acid, $R^2$ is a thiophene ring, $R^3$ is S, and $R^4$ is farnesyl.

(3)

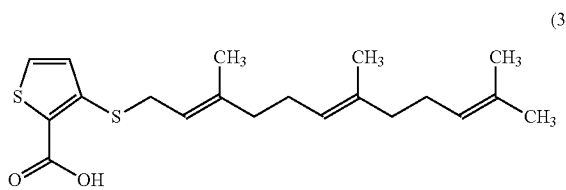

A preferred analog in this class is represented by N-methyl-3-{[(2E,6E)-3,7,11-trimethyldodeca-2,6,10-trien-1-yl]sulfanyl}thiophene-2-carboxamide (8) (shown below), which is similar to (3) above except that $R^1$ is a carboxylic acid N-Methyl amide.

(8)

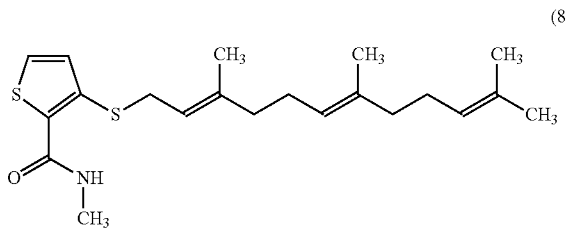 [SMILES: CNC(=O)c1sccc1SC/C=C(\C)CC/C=C(\C)CCC=C(C)C]

According to a second exemplary embodiment of the present disclosure, Formula (I) is further defined as set forth below:

$R^2$ represents a phenyl ring or an optionally substituted phenyl ring; and $R^1$ represents a 5- or 6-membered heterocyclic ring with at least one heteroatom, such as imidazoline, imidazole, pyrazole, pyrrole, oxazole, thiazole, or 1,4,5,6-tetrahydropyrimidine, or a 5-membered heterocyclic ring with multiple nitrogen atoms, such as triazole or $N(R^9)$-substituted tetrazole wherein:

$R^9$ represents hydrogen or C1-C4 alkyl;

the optionally substituted phenyl ring may be substituted with Cl, Br, F, I, C1-C4 alkyl, or C1-C4 alkoxy, amino, mono- or di-substituted amino; and the nitrogen substitutent on the phenyl ring is C1-C4 alkyl.

Based on this second exemplary embodiment, Formula (I) may include, for example, 2-(2-{[(2E,6E)-3,7,11-trimethyldodeca-2,6,10-trien-1-yl]sulfanyl}phenyl)-4,5-dihydro-1H-imidazole (5) (shown below) and its analogs, wherein $R^1$ is a 4,5-dihydro-1H-imidazole group, $R^2$ is a phenyl ring, $R^3$ is S, and $R^4$ is farnesyl.

(5)

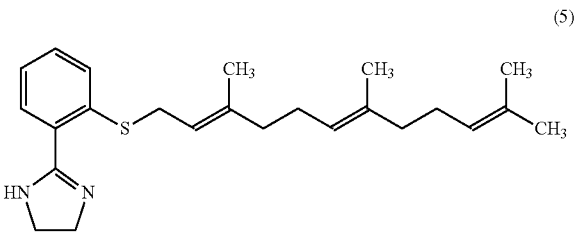 [SMILES: CC(C)=CCC/C(C)=C/CC/C(C)=C/CSc1ccccc1C1=NCCN1]

The structures of two preferred analogs in this class are described as follows:

(i) 1-methyl-2-(2-{[(2E,6E)-3,7,11-trimethyldodeca-2,6,10-trien-1-yl]sulfanyl}phenyl)-4,5-dihydro-1H-imidazole (6) (shown below), which is similar to (5) above except that the $R^1$ 4,5-dihydro-1H-imidazole group is substituted with a methyl group.

(6)

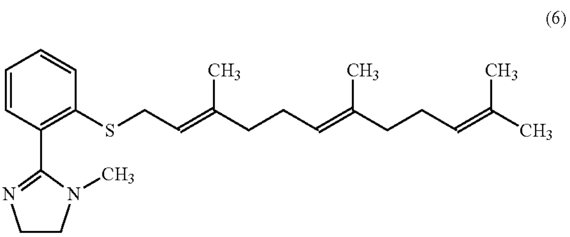 [SMILES: CC(C)=CCC/C(C)=C/CC/C(C)=C/CSc1ccccc1C1=NCCN1C]

(ii) 1-(propan-2-yl)-2-(2-{[(2E,6E)-3,7,11-trimethyldodeca-2,6,10-trien-1-yl]sulfanyl}phenyl)-4,5-dihydro-1H-imidazole (7) (shown below), which is similar to (5) above except that the $R^1$ 4,5-dihydro-1H-imidazole group is substituted with an isopropyl group.

(7)

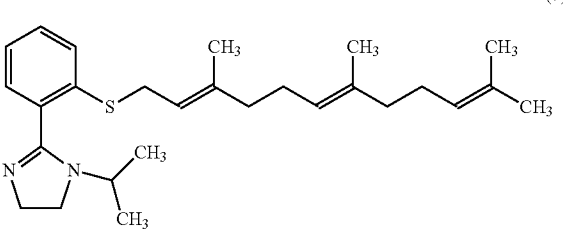

Based on this second exemplary embodiment, Formula (I) may also include, for example, 5-(2-{[(2E,6E)-3,7,11-trimethyldodeca-2,6,10-trien-1-yl]sulfanyl} phenyl)-2H-1,2,3,4-tetrazole (1) (shown below) and its analogs, wherein $R^1$ is a tetrazole group, $R^2$ is a phenyl ring, $R^3$ is S, and $R^4$ is farnesyl.

(1)

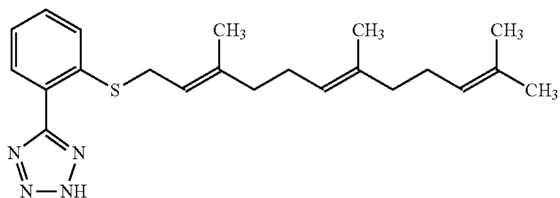

A preferred analog in this class is represented by 2-methyl-5-(2-{[(2E,6E)-3,7,11-trimethyldodeca-2,6,10-trien-1-yl] sulfanyl}phenyl)-2H-1,2,3,4-tetrazole and 1-methyl-5-(2-{[(2E,6E)-3,7,11-trimethyldodeca-2,6,10-trien-1yl] sulfanyl}phenyl)-1H-1,2,3,4-tetrazole (2) (shown below), which is similar to (1) above except that $R^1$ is a methyl-substituted tetrazole group.

(2)

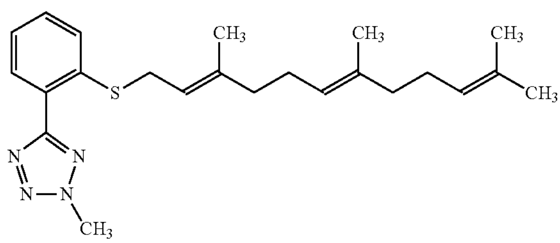

Based on this second exemplary embodiment, Formula (I) may also include, for example, 2-(2-{[(2E,6E)-3,7,11-trimethyldodeca-2,6,10-trien-1-yl]sulfanyl}phenyl)-1,4,5,6-tetrahydropyrimidine (9) (shown below) and its analogs, wherein $R^1$ is 1,4,5,6-tetrahydropyrimidine, $R^2$ is a phenyl ring, $R^3$ is S, and $R^4$ is farnesyl.

(9)

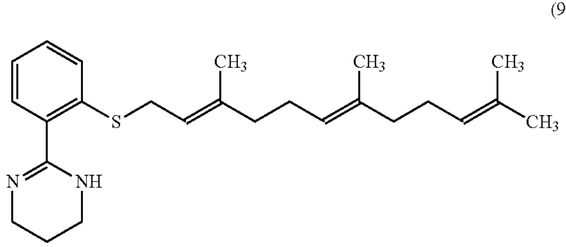

A preferred analog in this class is represented by 1-methyl-2-(2-{[(2E,6E)-3,7,11-trimethyldodeca-2,6,10-trien-1-yl] sulfanyl}phenyl)-1,4,5,6-tetrahydropyrimidine (10) (shown below), which is similar to (9) above except that the $R^1$ 1,4,5,6-tetrahydropyrimidine is substituted with a methyl group.

(10)

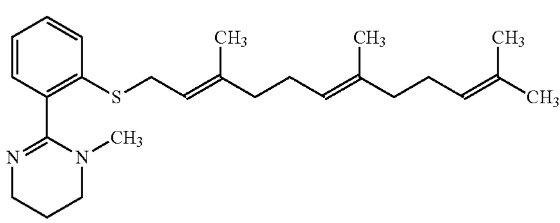

According to a third exemplary embodiment of the present disclosure, Formula (I) is further defined as set forth below:

$R^2$ represents a 5-membered heterocyclic ring with at least three heteroatoms, selected from O, N, and S, such as a thiadiazole group or an oxadiazole group; and $R^1$ represents C(=O)$R^{10}$, wherein $R^{10}$ represents hydrogen, hydroxyl, or C1-C4 alkyloxy.

Based on this third exemplary embodiment, Formula (I) may include, for example, Ethyl 5-{[(2E,6E)-3,7,11-trimethyldodeca-2,6,10-trien-1-yl]sulfanyl}-1,2,3-thiadiazole-4-carboxylate (4) (shown below) and its analogs, wherein $R^1$ is an ethyl-substituted carboxylate group, $R^2$ is 1,2,3-thiadiazole, $R^3$ is S, and $R^4$ is farnesyl.

(4)

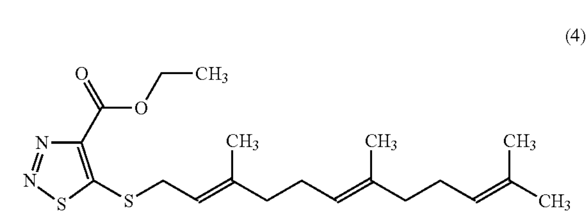 [SMILES: CCOC(=O)c1nnsc1SC/C=C(\C)CC/C=C(\C)CCC=C(C)C]

Based on this third exemplary embodiment, $R^1$ of Formula (I) may include carboxylic acid and $R^2$ of Formula (I) may include 1,2,3-oxadiazole or 1,2,5-oxadiazole, for example.

According to a fourth exemplary embodiment of the present disclosure, $R^1$ and $R^2$ both represent heterocyclic rings with at least one heteroatom. For example, $R^1$ may represent a 5- or 6-membered heterocyclic ring with at least one heteroatom, and $R^2$ may represent a 5-membered heterocyclic ring with at least one heteroatom.

The skilled artisan will appreciate that certain compounds of the present disclosure are not only useful as Ras inhibitors but are also useful intermediates for the preparation of additional compounds of the present disclosure. Methods for converting one chemical moiety to another will be recognized by skilled artisans. The skilled artisan will appreciate that not all of the substituents in the compounds of Formula (I) will tolerate certain reaction conditions employed to synthesize the compounds. These moieties may be introduced at a convenient point in the synthesis, or may be protected and then deprotected as necessary or desired. The skilled artisan will appreciate that the protecting groups may be removed at any convenient point in the synthesis of the compounds in the present disclosure. Such methods for introducing and removing these moieties are well known in the art. The skilled artisan will appreciate that in many circumstances, the order in which moieties are introduced may not be critical. The particular order of steps required to produce the compound of Formula (I) is dependent upon the particular compound being synthesized, the starting compound, and the relative lability or stability of the substituted moiety.

Oral administration of the compounds of the present disclosure is contemplated. However, oral administration is not the only route or even the preferred route. For example, transdermal administration, such as via a transdermal patch, may be desirable for patients suffering from a disease-like psoriasis. Transdermal may also be a preferred route of administration in cases where the patient may be forgetful or unable to take an oral formulation. The intravenous route may be preferred as a matter of convenience in a hospital setting or to avoid potential complications related to an oral dosage form. Compounds described in the present disclosure may be administered by percutaneous, intramuscular, intranasal, nasal, buccal, or intrarectal routes in particular circumstances. The route of administration may be varied in any way, limited by the physical properties of the compounds, the convenience of the patient and caregiver, and other relevant circumstances (Remington's Pharmaceutical Sciences, $18^{th}$ Edition, Mack Publishing Co. (1990)).

The pharmaceutical compositions of the present disclosure are prepared in a manner well known in the pharmaceutical art. The carrier or excipient may be a solid, semi-solid, or liquid material that can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like.

The compounds of the present disclosure may be administered orally, for example, with an inert diluent or capsules or compressed into tablets. For the purpose of oral administration, the compound may be incorporated with excipients and used in the form of tablets, troches, capsules, elixirs, suspensions, syrups, wafers, chewing gums, and the like. The preparations will contain a varied amount of active ingredient depending on the particular form and may be conveniently between 4% to about 70% of the weight of the unit. The amount of active ingredient present in the compositions is such that s suitable dosage will be obtained. Preferred compositions and preparations of the present invention may be determined by methods well known to the skilled artisan.

The tablets, pills, capsules, troches, and the like may also contain one or more of the following adjuvants: binders such as povidone, hydroxypropyl cellulose, microcrystalline cellulose, or gelatin; excipients or diluents such as: starch, lactose, microcrystalline cellulose or dicalcium phosphate, disintegrating agents such as: croscarmellose, crospovidone, sodium starch glycolate, corn starch and the like; lubricants such as: magnesium stearate, stearic acid, talc or hydrogenated vegetable oil; glidants such as colloidal silicon dioxide; wetting agents such as: sodium lauryl sulfate and polysorbate 80; and sweetening agents such as: sucrose, aspartame or saccharin may be added or a flavoring agent such as: peppermint, methyl salicyclate or orange flavoring. When the dosage unit form is a capsule, it may contain, in addition to materials of the above type, a liquid carrier such as polyethylene glycol or a fatty oil. Other dosage unit forms may contain other various materials that modify the physical for of the dosage unit, for example, as coatings. Thus, tablets or oils may be coated with sugar, hydroxypropylmethyl cellulose, polymethacrylate, or other coating agents. Syrups may contain in addition to the present compounds, sucrose as a sweetening agent and certain preservatives, dyes, colorings and flavors. Materials used in preparing these various compositions should be pharmaceutically pure and non-toxic in the amount used.

The compounds of the present disclosure are generally effective over a wide dosage range. For example, dosages per day normally fall within the range of about 0.0001 to about 30 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstance, including the condition to be treated, the chosen route of administration, the actual compound or compounds administered, the age, weight, and response of the individual patient, and the severity of the patient's symptoms.

It will be appreciated by those knowledgeable in the area that numerous treatment options exist to treat the diseases encompassed in this disclosure. For example, anti-cancer therapy includes chemotherapy, radiation therapy, immunotherapy or gene therapy, and combinations thereof. Chemotherapy refers to existing medication administered to patients with a particular disease. The skilled artisan will recognize the value of adding the compounds described in the current disclosure to existing treatment options. The combination of existing treatment options and the compounds described in the present disclosure will have particular value in the Ras-driven diseases described herein. Examples of chemotherapeutic agents include, but are not limited to, paclitaxel (Taxol®), docetaxel (Taxotere®), cisplatin, carboplatin (Paraplatin®), gemcitabine hydrochloride (Gemzar®), doxorubicin hydrochloride, etoposide (Etopophos®, Vepesid®), pemetrexed (Alimta®), topotecan (Hycamtin®), vinblastine (Velbe®), Vindesine (Eldisine®), vinorelbine (Navelbine®), ifosfamide (Mitoxana®), and Mitomycin. Examples of chemotherapeutic agents for non-malignant diseases described herein include, but are not limited to, glatiramer acetate (Copaxone), metformin (Gkucophage), chloroquin, 2-deoxy-glucose, sodium valproate, cholesterol, statins, and clopidogrel (Plavix®).

EXAMPLES

The following examples illustrate methods of producing and using the Ras antagonists of the present disclosure.

1. Example 1

Preparation of 5-(2-{[(2E,6E)-3,7,11-trimethyl-dodeca-2,6,10-trien-1-yl]sulfanyl}phenyl)-2H-1,2,3,4-tetrazole (1)

A. Step 1(A): Preparation of 2-(benzylthio)benzonitrile

A mixture consisting 2-nitrobenzenenitrile (5.0 g, 33.75 mmol) in 30 mL of anhydrous dimethylformamide (DMF) was cooled in an ice water bath (0° C.) and placed under $N_2$ atmosphere. Benzylmercaptan (4.0 mL, 33.75 mmol) was added followed by the dropwise addition of an aqueous potassium hydroxide solution (3.40 g, 60.75 mmol in 10 mL of water). The reaction mixture was stirred at 0° C. for thirty minutes then allowed to warm to room temperature. After four hours the reaction appeared complete by thin layer chromatography (TLC). To the reaction mixture ice water (100 mL) was added. The solution was extracted with dichloromethane (200 mL) and washed with brine (100 mL). The organic layer was dried over sodium sulfate ($Na_2SO_4$) and then concentrated under reduced pressure to afford a red oil. The product was purified by flash silica column chromatography. Elution through an 80-g Silicycle® flash silica cartridge with 5% ethyl acetate in heptanes afforded the title compound as a bright yellow solid (6.08 g, 80%) $R_f$ of 0.24" with 95:5 v/v heptanes: ethyl acetate; $^1$H-NMR (400 MHz; $CDCl_3$) δ 7.62 (dd, 1H), 7.47-7.42 (dt, 1H), 7.38 (dd, 1H), 7.32-7.25 (m, 6H); MS (ESI−) m/z 224.1 (Mz−1).

B. Step 1(B): Preparation of 2-mercaptobenzonitrile

In a 3-neck round bottom flask that contained an addition funnel was added benzene (40 mL). The flask was placed under $N_2$ atmosphere and cooled in an ice water bath (0° C.). Aluminum chloride (4.88 g, 36.61 mmol) was added to the benzene solution. A solution of 2-(benzylthio)benzonitrile (5.0 g, 22.19 mmol) from Step 1(A) in benzene (40 mL) was added to the addition funnel. The solution was added dropwise over forty minutes and the reaction mixture was stirred at 0° C. for one hour and then stirred at room temperature for 48 hours. The reaction was worked up by pouring the crude mixture into ice water (200 mL) and stirring for 30 minutes. 10% NaOH (100 mL) solution was added and the mixture was stirred for 10 minutes. The solution was acidified (pH=2) by addition of 6N hydrochloric acid (HCl). The solution was placed in a separatory funnel and extracted with dichloromethane (3×100 mL). The combined organics were dried over $Na_2SO_4$ and then concentrated under reduced pressure to afford a brown oil. The product was purified by flash silica column chromatography. Elution through an 80-g Silicycle® flash silica cartridge with 5% ethyl acetate in heptanes afforded the title compound as a brown oil (2.55 g, 85%); $R_f$ of 0.56" with 70:30 v/v heptanes: ethyl acetate; $^1$H-NMR (400 MHz; $CDCl_3$) δ 7.52 (d, 1H), 7.39-7.32 (m, 2H), 7.19-7.14 (m, 1H), 4.01 (s, 1H); MS (ESI−) m/z 134.05 (Mz−1).

C. Step 1(C): Preparation of 2-(2H-tetrazol-5-yl)benzenethiol

In a 250 mL round bottom flask was added 2-mercaptobenzonitrile (2.0 g, 14.8 mmol) from Step 1(B) followed by anhydrous DMF (30 mL). Ammonium chloride (1.42 g, 26.64 mmol) and sodium azide (1.73 g, 26.64 mmol) were added to the reaction flask followed by an additional 10 mL of DMF. The reaction mixture was heated to 105° C. under a flow of $N_2$ and stirred overnight. The reaction was worked up by first cooling to room temperature. Next the solution was acidified by the addition of 50 mL of 1N HCl. The solution was extracted with ethyl acetate (2×100 mL) and then washed with brine (100 mL). The combined organics were dried over $Na_2SO_4$ and then concentrated under reduced pressure to afford a white solid. The solid was collected by filtration of a heptane/ethyl acetate treatment (7:3, 10 mL) which afforded the title compound as a white solid (1.21 g, 46%); $R_f$ of 0.05" with 95:5 v/v dichloromethane: methanol; $^1$H-NMR (400 MHz; DMSO-$d_6$) δ 7.91 (d, 1H), 7.78 (d, 1H), 7.64-7.50 (m, 2H), 2.90 (s, 1H), 2.78 (s, 1H); MS (ESI−) m/z 177.1 (Mz−1).

D. Step 1(D): Final preparation of 5-(2-{[(2E,6E)-3,7,11-trimethyldodeca-2,6,10-trien-1-yl]sulfanyl}phenyl)-2H-1,2,3,4-tetrazole (1)

In a scintillation vial, 2-(2H-tetrazol-5-yl)benzenethiol (0.150 g, 0.842 mmol) from Step 1(C) was weighed. The solid was dissolved in 10 mL of acetone and 1 mL of anhydrous DMF. Guanidine carbonate (0.379 g, 2.105 mmol) and trans, trans-farnesylbromide (0.24 mL, 0.884 mmol) were added to the reaction flask. The reaction mixture was heated to 40° C. under a flow of $N_2$ and stirred overnight. The reaction was worked up by first cooling to room temperature. The reaction mixture was diluted with dichloromethane (100 mL) and then washed with 1N HCl (50 mL). The organics were then washed with brine (100 mL) and then dried over $Na_2SO_4$ and concentrated under reduced pressure to afford a crude oil. The product was purified by flash silica column chromatography. Elution through an 12-g Silicycle® flash silica cartridge with (5-15%) ethyl acetate in heptanes afforded the title compound as an oil (32.5 mg, 10%); $R_f$ of 0.64" with 50:50 v/v heptanes: ethyl acetate; $C_{22}H_{30}N_4S_1$ mol. wt. 382.57 g/mol, $^1$H-NMR (400 MHz; $CDCl_3$) δ 7.72 (d, 1H), 7.55 (t, 1H), 7.40 (t, 1H), 7.30 (d, 1H), 5.20 (t, 1H), 5.10 (t, 1H), 5.05 (t, 1H), 4.81 (d, 2H), 2.10-1.95 (m, 8H), 1.71 (s, 3H), 1.62-1.55 (m, 6H), 1.43 (s, 3H); MS (APCI+) m/z 383.2, 765.4 (Mz+1, 2Mz+1).

2. Example 2

Preparation of 2-methyl-5-(2-{[(2E,6E)-3,7,11-trimethyldodeca-2,6,10-trien-1-yl]sulfanyl}phenyl)-2H-1,2,3,4-tetrazole and 1-methyl-5-(2-{[(2E,6E)-3,7,11-trimethyldodeca-2,6,10-trien-1-yl]sulfanyl}phenyl)-1H-1,2,3,4-tetrazole (2)

In a scintillation vial, sodium hydride (60% dispersion in mineral oil, 5.0 mg) was weighed. Anhydrous DMF (1 mL) was added followed by iodomethane (0.01 mL). The reaction mixture was stirred for five minutes then compound (1) (0.040 g, 0.105 mmol) from Step 1(D) was added dropwise as a solution in DMF (2 mL). The reaction was stirred at room temperature for 1 hour, where it was determined by TLC to be complete. The reaction was worked up by addition of water (6 mL). The solution was extracted with ethyl acetate (50 mL) and then dried over magnesium sulfate ($MgSO_4$), filtered, and concentrated to afford a crude oil. The product was purified by flash silica column chromatography. Elution through a 12-g Silicycle® flash silica cartridge with gradient (2-20%) ethyl acetate in heptanes afforded the title compound as a colorless oil (15.6 mg, 38%). $C_{23}H_{33}N_4S_1$ mol. wt. 397.60 g/mol, $R_f$ of 0.68" with 50:50 v/v heptanes: ethyl acetate; MS (APCI+) m/z 397.1 (Mz). $^1$H NMR was taken of mixed fraction which showed product formation (N—$CH_3$). $^1$H-NMR (400 MHz; $CDCl_3$) δ 3.85 (s, 3H).

3. Example 3

Preparation of 3-{[(2E,6E)-3,7,11-trimethyldodeca-2,6,10-trien-1-yl]sulfanyl}thiophene-2-carboxylic acid (3)

3-Sulfenyl-2-thiophene carboxylic acid (50 mg, 0.31 mmol) was dissolved in acetone (5 mL). Guanidine Carbonate (66 mg, 0.38 mmol) was added followed by dropwise addition of trans,trans-farnesylbromide (88.5 mg, 0.31 mmol) at room temperature, and the mixture was stirred overnight. The reaction mixture was evaporated and was suspended in chloroform (20 mL) and acidified with 2N HCl. The reaction mixture was washed with water (10 mL) followed by brine. The reaction mixture was dried over 5 g of saturated $Na_2SO_4$, filtered, and the filtrate was evaporated at reduced pressure. The crude reaction mixture was purified on normal silica gel column (2 cm×31 cm) using 30:70 ethyl acetate:hexane. The first fraction of 100 mL was collected in an Erlenmeyer flask and subsequently 7 mL fractions were collected. All the fractions were checked by TLC. Fractions with pure product were combined and evaporated. Yield 58 mg (50.9%), $R_f$ of 0.47" in 40:60 ethyl acetate:hexane; $C_{20}H_{28}O_2S_2$, mol. wt. 364.6 g/mol, ES/M-H+363, UV $\lambda_{max}$ 268, 314 nm.

4. Example 4

Preparation of Ethyl 5-{[(2E,6E)-3,7,11-trimethyldodeca-2,6,10-trien-1-yl]sulfanyl}-1,2,3-thiadiazole-4-carboxylate (4)

Ethyl-5-mercapto-1,2,3-thiazdazole-4-Carboxylate (50 mg, 0.26 mmol) was dissolved in acetone (5 mL). Guanidine Carbonate (56 mg, 0.31 mmol) was added followed by dropwise addition of trans,trans-farnesylbromide (71 mg, 0.31 mmol) at room temperature, and the mixture was stirred overnight. The reaction mixture was evaporated and was suspended in chloroform (20 mL) and acidified with 2N HCl. The reaction mixture was washed with water (10 mL) followed by brine (20 mL). The reaction mixture was dried over 5 g of saturated $Na_2SO_4$, filtered, and the filtrate was evaporated at reduced pressure. The crude reaction mixture was purified on normal silica gel column (2 cm×35 cm) using 5:95 acetone:hexane. The first fraction of 100 mL was collected in an Erlenmeyer flask and subsequently 7 mL fractions were collected. All the fractions were checked by TLC. Fractions with pure product were combined and evaporated. Yield 41 mg (39.4%), $R_f$ of 0.51" in 10:90 ethyl acetate:hexane; $C_{20}H_{30}N_2O_2S_2$ mol. wt. 394.6 g/mol, APC/MH+394.9, UV $\lambda_{max}$ 303 nm.

5. Example 5

Preparation of 2-(2-{[(2E,6E)-3,7,11-trimethyl-dodeca-2,6,10-trien-1-yl]sulfanyl}phenyl)-4,5-dihydro-1H-imidazole (5)

2-(4,5-Dihydro-1H-imidazole-2-yl)benzenethiol (50 mg, 0.28 mmol) was dissolved in acetone (6 mL). Guanidine Carbonate (58.6 mg, 0.32 mmol) was added followed by dropwise addition of trans,trans-farnesylbromide (75.6 mg, 0.28 mmol) at room temperature, and the mixture was stirred overnight. The reaction mixture was evaporated and was suspended in chloroform (20 mL) and acidified with 2N HCl. The reaction mixture was washed with water (10 mL) followed by brine (20 mL). The reaction mixture was dried over 5 g of saturated $Na_2SO_4$, filtered, and the filtrate was evaporated at reduced pressure. The crude reaction mixture was purified on normal silica gel column (2 cm×31 cm) using 10:90 ethanol:ethyl acetate. The first fraction of 100 mL was collected in an Erlenmeyer flask and subsequently 7 mL fractions were collected. The solvent gradient was increased slowly to 50:50 ethanol:ethyl acetate. All the fractions were checked by TLC. Fractions with pure product were combined and evaporated. Yield 40 mg (37.2%), $R_f$ of 0.4" in 85:15:2 chloroform:methanol: water.

6. Example 6

Inhibition of U87MG and PANC-1 Cell Proliferation

The ability of the compounds of the present invention to inhibit cell growth is demonstrated by standard assays known to the skilled artisan, and are briefly described in the following paragraphs.

A. Step 6(A): Cell Culture

The adult glioblastoma cell line U87MG was obtained from a commercial source (ATCC). The pancreatic cancer cell line PANC-1 was obtained from a local laboratory (Indiana University). Both lines were grown in Iscove's Modified Dulbecco's Medium with 10% fetal bovine serum (FBS) at 37° C. and 5% $CO_2$.

B. Step 6(B): Sample Preparation

Compounds (1), (2), (3), (4), and (5), which are shown and described above, were each dissolved in ethanol at 10 mg/mL. A measured portion of the solution was pipetted into a microcentrifuge tube. Then, the ethanol was evaporated from each tube using a SpeedVac®, leaving just the compound in the tube. The appropriate amount of chloroform was added to the tube to produce a 0.1M concentration. The solutions were placed on ice and in the dark so they could be pipetted into 10- and 20-μL aliquots in 1.5 mL microcentrifuge tubes. The solutions were frozen at 80° C. with lids closed tightly and the tubes covered with foil.

Prior to treating the cells, a tube of the test compound was removed from the freezer and placed under a biosafety hood to evaporate the chloroform in the tubes. Then, dimethyl sulfoxide (DMSO) was added to the tubes to make the correct concentration to use in the experiment (0.1M stock). The tubes were vortexed, and warm media with 10% FBS was slowly added to make the correct working concentrations to be used in the experiment. The compounds were directly added to each well for treatment.

For reference, similar samples were prepared of farnesylthiosalicylic acid (FTS) (shown below). FTS is the subject of U.S. Pat. No. 5,705,528 to Kloog.

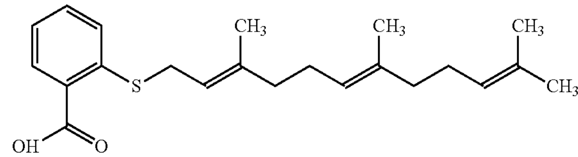 [SMILES: CC(C)=CCC/C(C)=C/CC/C(C)=C/CSc1ccccc1C(=O)O]

C. Step 6(C): Cell Proliferation Assay for U87MG Cells

U87MG cells were seeded in a 24-well plate, 5000 cells per well, and incubated overnight at 37° C. in serum-free media. The next day they were treated in triplicate with 50 and 100 μM of each test compound (1), (2), (3), (4), and (5) and the reference compound FTS. After five days, the cells were trypsinized (0.5%), stained with trypan blue, and counted to determine the cell number per well. The $IC_{50}$ values were calculated using Multiplex Reader-Fit software made by MiraiBio Group, Hitachi Solutions America, Ltd. In a typical experiment, the control wells averaged 138,000 cells. The results are presented graphically in FIG. 1. The test compounds at 50 μM allowed the following U87MG cell proliferation compared to control: compound (1)—37%, compound (2)—18%, compound (3)—10%, compound (4)—40%, and compound (5)—0%. The reference compound FTS at 50 μM allowed 7% cell proliferation compared to control.

Figure 2:
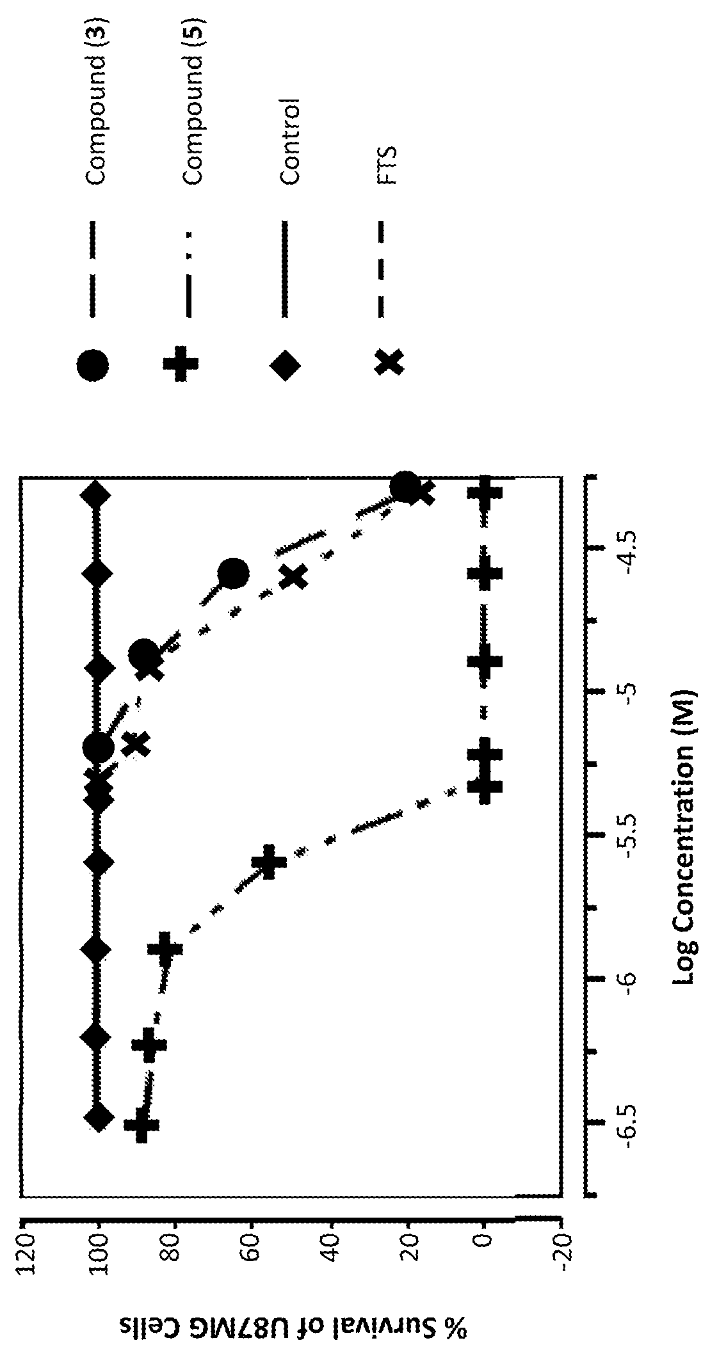
FIG. 2 is a graph illustrating the inhibition of U87MG cell proliferation relative to a control sample when exposed to certain inventive compounds in various doses less than those of FIG. 1.

To further evaluate compounds (3) and (5), which inhibited the most cell growth in FIG. 1, more U87MG cells were seeded in 24-well plates, 5000 cells per well, and incubated overnight at 37° C. in serum-free media. The cells were treated the next morning in media with 5% serum in triplicate with standard concentrations of 6.25, 12.5, 25, and 50 μM of each test compound (3) and (5) and the reference compound FTS. After five days of treatment, the cells were trypsinized (0.5%) and then stained with trypan blue. Cells were counted to determine the number of cells per well. Again, the $IC_{50}$ values were calculated using Multiplex Reader-Fit software made by MiraiBio Group, Hitachi Solutions America, Ltd. In a typical experiment, the control wells averaged 56,000 cells. The results are presented graphically in FIG. 2. The test compounds at 25 μM allowed the following U87MG cell proliferation compared to control: compound (3)—69% and compound (5)—0%. The reference compound FTS at 25 μM allowed over 50% cell proliferation compared to control.

Since the doses of compound (5) used above killed all of the cells, the dose curve was set up again using even lower doses of compound (5). U87MG cells were seeded in 24-well plates, 5000 cells per well, and incubated overnight at 37° C. in serum-free media. The cells were treated in triplicate with 6.25, 12.5, 25, and 50 μM of the reference compound FTS and 0.3125, 0.625, 1.25, 2.5, and 5.0 μM of the test compound (5) in media with 5% serum for five days. Then, the cells were trypsinized (0.5%) and stained with trypan blue, and the cell number per each well was determined. Again, the $IC_{50}$ values were calculated using Multiplex Reader-Fit software made by MiraiBio Group, Hitachi Solutions America, Ltd. In a typical experiment, the control wells averaged 58,000 cells. The results are presented graphically in FIG. 2. The test compound (5) at 2.5 μM allowed 56% U87MG cell proliferation compared to control. Even at a higher dose of 6.25 μM, the reference compound FTS allowed over 80% cell proliferation compared to control.

D. Step 6(D): Cell Proliferation Assay for PANC-1 Cells

Figure 3:
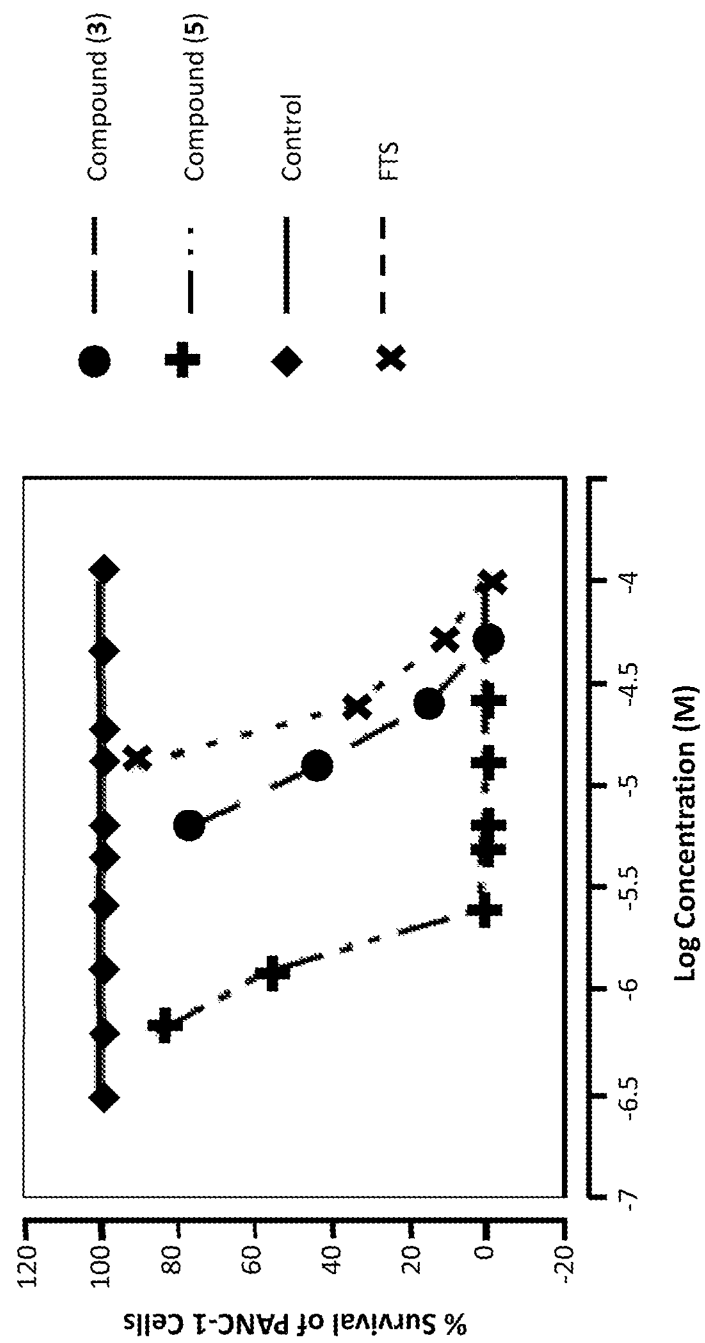
FIG. 3 is a graph illustrating the inhibition of PANC-1 cell proliferation relative to a control sample when exposed to certain inventive compounds of the present disclosure in various doses.

The $IC_{50}$ values for PANC-1 cells were determined by seeding the cells in 24-well plates, 7500 cells per well, and incubating them overnight at 37° C. in serum-free media. The cells were treated in triplicate with standard concentrations of 6.25, 12.5, 25, 50, and 100 μM of each test compound (3) and (5) and the reference compound FTS and, when needed, concentrations of 0.625, 1.25, 2.5 and 5.0 μM in media with 5% serum for five days. Then, the cells were stained with trypan blue, and the cell number per each well was determined. Again, the $IC_{50}$ values were calculated using Multiplex Reader-Fit software made by MiraiBio Group, Hitachi Solutions America, Ltd. In a typical experiment, the control wells averaged 32,500 cells. The results are presented graphically in FIG. 3. Test compound (3) at 12.5 μM allowed 41% PANC-1 cell proliferation compared to control, and test compound (5) at 1.25 μM allowed 56% PANC-1 cell proliferation compared to control. Even at 12.5 μM, the reference compound FTS allowed over 80% cell proliferation compared to control.

7. Example 7

Human Hematopoietic Progenitor Cell Toxicity

Cord blood low density cells were plated at $1\times10^5$ cells per plate in 1 mL complete methylcellulose in the presence of each test compound (3) and (5) and incubated for 12 days in a $CO_2$ incubator. Colony-forming unit-granulocyte (CFU-GM), burst-forming unit-erythroid (BFU-E), and mixed colonies were counted under an inverted microscope. The test compounds were used at the $IC_{50}$ and $IC_{0.5}$ values, 25 and 2.5 μM for compound (3), and 2.5 and 0.25 μM for compound (5) as determined on the U87MG cells previously. The test compounds were not toxic to the hematopoietic progenitor cells.

8. Example 8

Ras Activation and Cell Proliferation in Mast Cells

Figure 4A:
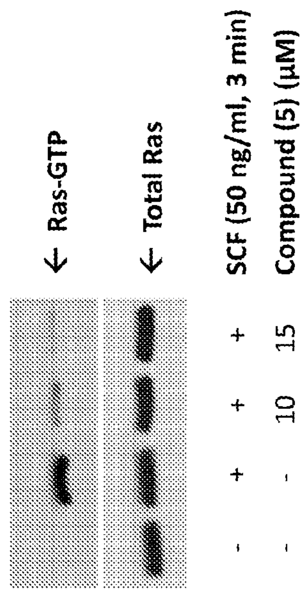
FIG. 4A is a Western blot illustrating the inhibition of activated RAS in mast cells relative to a control sample when exposed to an inventive compound of the present disclosure in various doses.
Figure 4B:
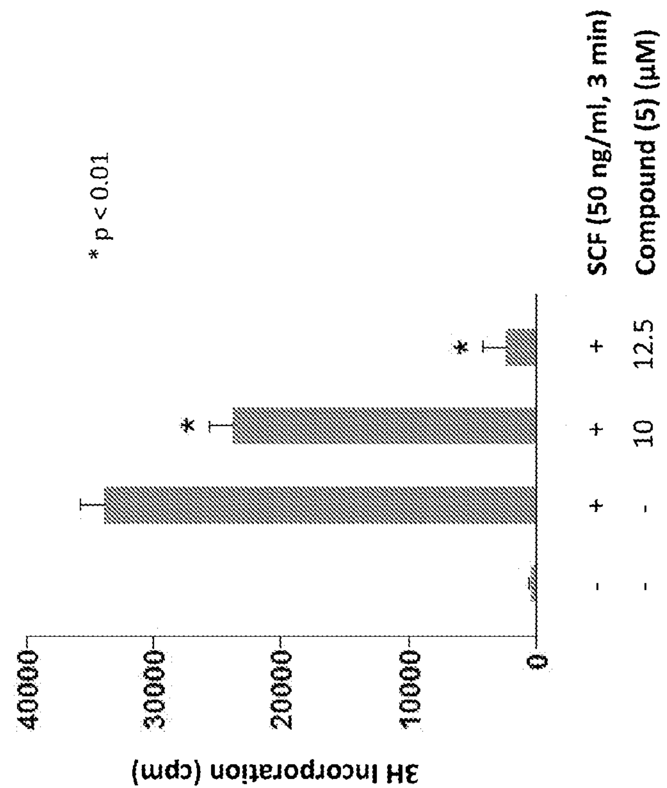
FIG. 4B is a graph illustrating the inhibition of mast cell proliferation relative to a control sample when exposed to an inventive compound of the present disclosure in various doses.

Purified populations of NF-1+/−mast cells were stimulated with a maximum stimulating concentration of stem cell factor (SCF) in the presence of a control or compound (5) at concentrations of 10-15 μM. The activated, GTP-bound form of Ras (Ras-GTP) was measured 3 minutes subsequently using Western blot analysis. The results are presented in FIG. 4A, which shows that compound (5) significantly reduced the level of Ras-GTP relative to the control. In parallel experiments, mast cell proliferation was measured using 3H-thymidine incorporation 24 hours after SCF stimulation in the presence of a control or compound (5) at concentrations of 0-12.5 μM. The results are presented in FIG. 4B, which shows that compound (5) reduced mast cell proliferation relative to the control. Each asterisk in FIG. 4B represents a statistical difference relative to the control using analysis of variance. (Yang, Feng-Chun, et. al. J Clin Invest 2003, 112(12), 1851-1861; Yang, Feng-Chun, et. al. Hum Mol Genet. 2006, 15(11), 1921-1930).

9. Example 9

Ras Activation and Cell Proliferation in Schwann Cells

Figure 5B:
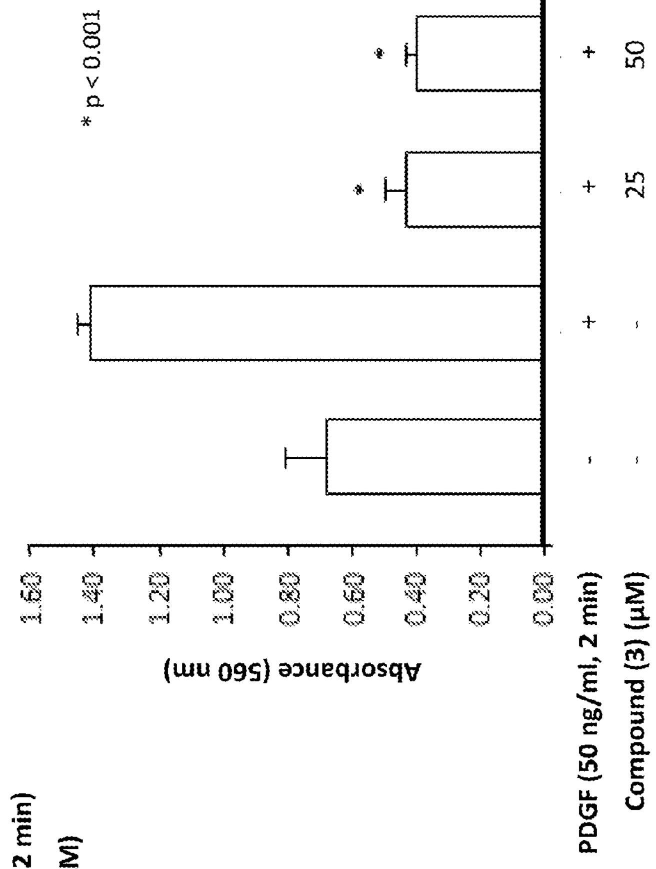
FIG. 5B is a graph illustrating the inhibition of Schwann cell proliferation relative to a control sample when exposed to an inventive compound of the present disclosure in various doses.
Figure 5A:
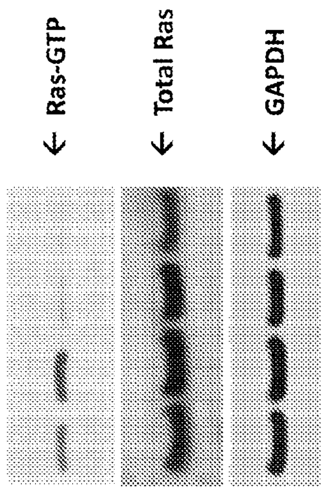
FIG. 5A is a Western blot illustrating the inhibition of activated RAS in Schwann cells relative to a control sample when exposed to an inventive compound of the present disclosure in various doses.

A purified population of NF-1−/− S 100+ Schwann cells isolated from a plexiform neurofibroma in a genetically engineered mouse (Zhu, Y. et al., Science, May 2002, 3; 296 (5569)):920-922) were stimulated with a maximum stimulating concentration of platelet derived growth factor (PDGF) in the presence of a control or compound (3) at concentrations of 2.5-5 μM. Ras-GTP was measured 3 minutes subsequently using Western blot analysis. The results are presented in FIG. 5A, which shows that compound (3) significantly reduced the level of Ras-GTP relative to the control. In parallel experiments, Schwann cell proliferation was measured using visible spectroscopy 24 hrs after PDGF stimulation in the presence of a control or compound (3) at concentrations of 25-50 μM. The results are presented in FIG. 5B, which shows that compound (3) reduced Schwann cell proliferation relative to the control. Each asterisk in FIG. 5B represents a statistical difference relative to the control using analysis of variance. (Yang, Feng-Chun, et. al. J Clin Invest 2003, 112(12), 1851-1861; Yang, Feng-Chun, et. al. Hum Mol Genet. 2006, 15(11), 1921-1930).

The compounds disclosed herein have been shown to limit Ras activation and the proliferation of tumorigenic cells, which is central to the disease pathogenesis of multiple NF-1 sequelae. By limiting the proliferation of tumorigenic cells, the compounds disclosed herein may limit such NF-1 sequelae.

Preferred Ras antagonists of the present disclosure include compounds (3) and (5). A particularly preferred Ras antagonist is compound (5). Other Ras antagonists useful in the present disclosure may be identified by using the cell free membrane assays and cellular assays described in WO 98/38509, the disclosure of which is expressly incorporated herein by reference in its entirety. This patent publication describes several assay systems designed to determine the ability of a candidate agent to dislodge activated Ras from its membrane. In general, the assay material that contains specific membranes having a known and detectable quantity of Ras anchored thereto is exposed to the candidate agent. The assay material is then separated into a membrane fraction containing the membranes and a cytosolic fraction of a balance of the material remaining after the specific membranes are removed. A fraction of the known quantity of the labeled Ras contained in the membrane and cytosolic fraction is determined as a measure of the ability of the candidate agent to disrupt membrane association of Ras. A particularly convenient source of activated Ras-anchored membranes is membranes isolated from Ras transformed cancer cells such as PANC-1 cells.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A compound represented by the Formula (I) or a salt of the Formula (I):

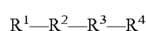

$$R^1—R^2—R^3—R^4 \quad (I)$$

wherein:

$R^1$ represents a 5- or 6-membered heterocyclic ring with at least one heteroatom;

$R^2$ represents an optionally substituted phenyl ring;

$R^3$ represents S, O, a substituted N, SO, $SO_2$, or Se; and $R^4$ represents farnesyl or geranyl-geranyl.

2. The compound of claim 1, wherein $R^1$ represents imidazoline, imidazole, pyrazole, pyrrole, oxazole, thiazole, 1,4,5,6-tetrahydropyrimidine, triazole, or N($R^9$)-substituted tetrazole; and wherein:

$R^9$ represents hydrogen or C1-C4 alkyl;

the optionally substituted phenyl ring is substituted with Cl, Br, F, I, C1-C4 alkyl, or C1-C4 alkoxy, amino, mono- or di-substituted amino; and the nitrogen substitutent on the phenyl ring is C1-C4 alkyl.

3. The compound of claim 1 having the formula (5):

(5)

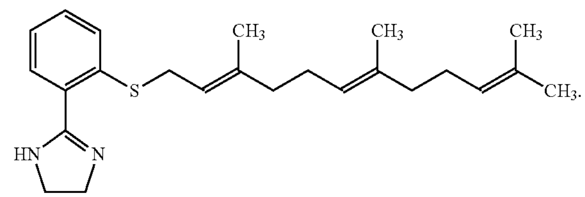

4. The compound of claim 1 having the formula (1):

(1)

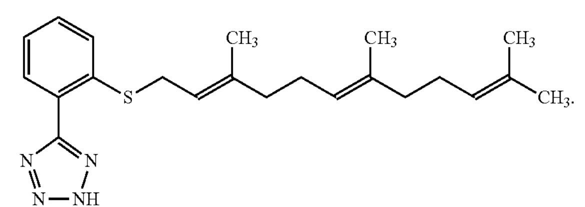

5. The compound of claim 1 having the formula (9):

(9)

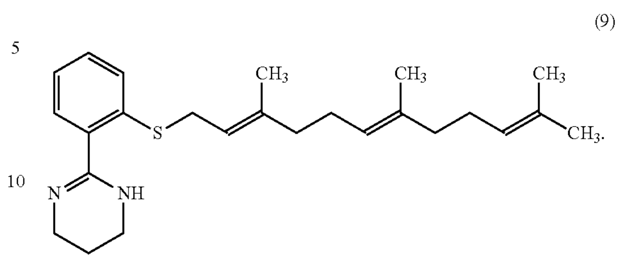

6. The compound of claim 1, wherein the salt is a salt of formula (5):

(5)

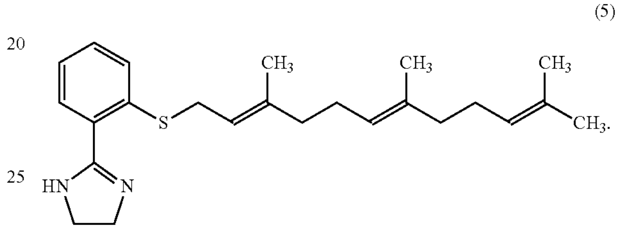

7. The compound of claim 1 having the formula (6):

(6)

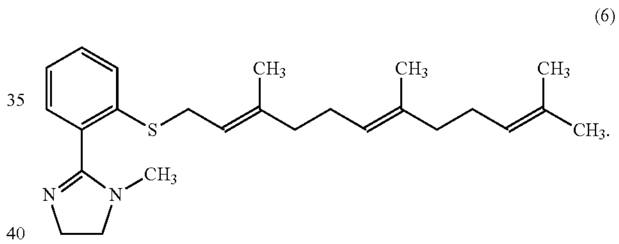

8. The compound of claim 1, wherein the salt is a salt of formula (6):

(6)

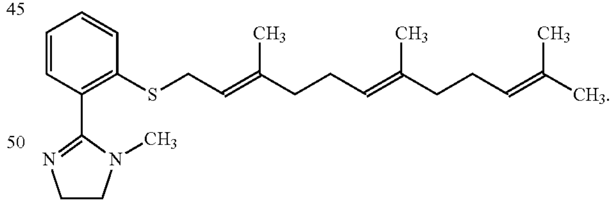

9. The compound of claim 1 having the formula (7):

(7)

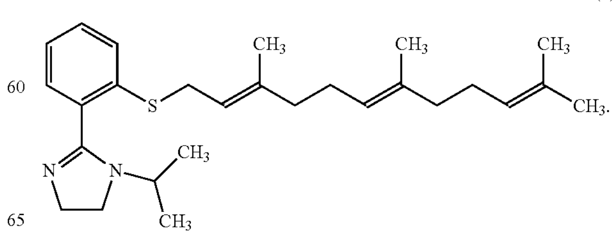

10. The compound of claim 1, wherein the salt is a salt of formula (7):

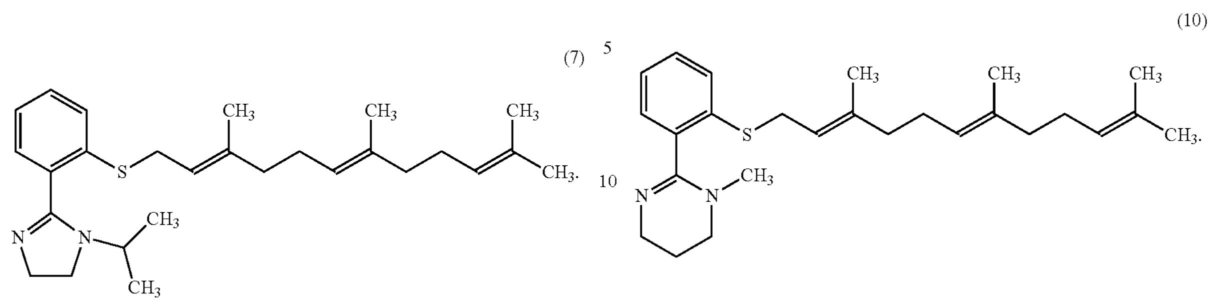

11. The compound of claim 1 having the formula (2):

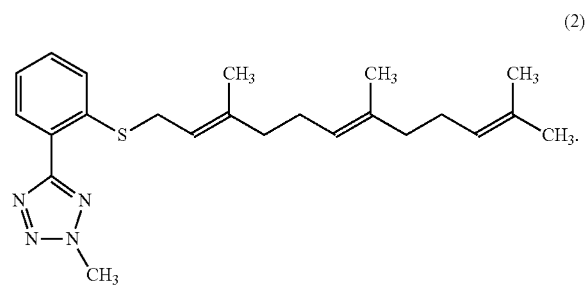 [SMILES: CC(C)=CCC/C(C)=C/CC/C(C)=C/CSc1ccccc1-c1nnn(C)n1]

12. The compound of claim 1 having the formula (10):

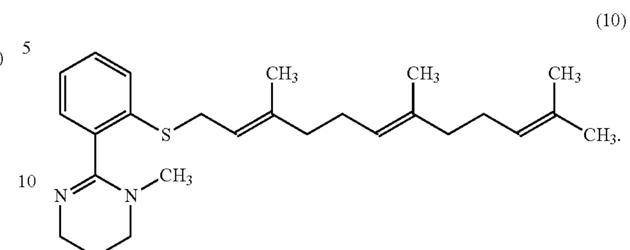

13. A method of treating glioblastoma, the method comprising:

administering to a patient the compound of claim 1 in an amount effective to inhibit proliferation of cells associated with glioblastoma.

14. A method of treating pancreatic cancer, the method comprising:

administering to a patient the compound of claim 1 in an amount effective to inhibit proliferation of cells associated with pancreatic cancer.

15. A method of inhibiting Ras-induced proliferation of cells associated with glioblastoma, the method comprising:

contacting the cells with the compound of claim 1 in an amount effective to inhibit the proliferation.

16. A method of inhibiting Ras-induced proliferation of cells associated with pancreatic cancer, the method comprising:

contacting the cells with the compound of claim 1 in an amount effective to inhibit the proliferation.

* * * * *